United States Patent
Schlosser et al.

[11] Patent Number: 5,716,543
[45] Date of Patent: Feb. 10, 1998

[54] 3,4,5-TRIFLUOROBENZENES, AND THEIR USE IN LIQUID-CRYSTAL MIXTURES

[75] Inventors: Hubert Schlosser, Glashütten; Dietmar Jungbauer, Weiterstadt, both of Germany

[73] Assignee: Merck Patent Gesellschaft mit beschrankter Haftung, Darmstadt, Germany

[21] Appl. No.: 624,490

[22] PCT Filed: Sep. 26, 1994

[86] PCT No.: PCT/EP94/03212

§ 371 Date: Apr. 4, 1996

§ 102(e) Date: Apr. 4, 1996

[87] PCT Pub. No.: WO95/10498

PCT Pub. Date: Apr. 20, 1995

[30] Foreign Application Priority Data

Oct. 8, 1993 [DE] Germany .................. 43 34 363.5

[51] Int. Cl.⁶ .................. C09K 19/30; C09K 19/34; G02F 1/13
[52] U.S. Cl. .................. 252/299.63; 252/299.61; 252/299.66; 252/299.67; 252/299.01; 349/182
[58] Field of Search .................. 252/299.61, 299.62, 252/299.63, 299.66, 299.67; 349/182

[56] References Cited

U.S. PATENT DOCUMENTS 5,032,313  7/1991  Goto et al. .................. 252/299.63
5,487,845  1/1996  Reiffenrath et al. .................. 252/299.63

FOREIGN PATENT DOCUMENTS 423520  4/1991  European Pat. Off. .

Primary Examiner—Shean C. Wu
Attorney, Agent, or Firm—Millen, White, Zelano, & Branigan, P.C.

[57] ABSTRACT

A 3,4,5-trifluorobenzene derivatives of formula (I):

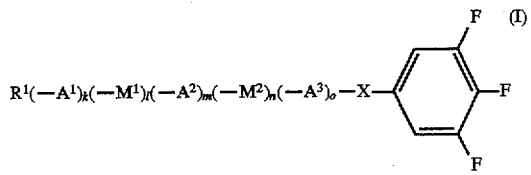

in which $R^1$ is a straight-chain or branched alkyl having 1 to 15 carbon atoms in which one or two nonadjacent —$CH_2$—groups are optionally replaced by —O—, —CH=CH—, —C≡C—, cyclopropane-1,2-diyl or —$Si(CH_3)_2$—, and in which one or more H atoms in the alkyl radical may be substituted by F; $A^1$, $A^2$ and $A^3$ are identical or different 1,4-phenylene, pyridine-2,5-diyl, pyrimidine-2,5-diyl in which one or two H atoms are, optionally, replaced by F, trans-1,4-cyclohexylene, 1,3-dioxane-2,5-diyl or naphthalene-2,6-diyl, $M^1$ and $M^2$ are identical or different —$CH_2CH_2$—,—CH=CH—,—C≡C—,—$CH_2CH_2CH_2CH_2$—, —$CH_2$—O—,—O—$CH_2$—,—CO—O— or —O—CO; X is —$CH_2$—O—,—$OCH_2$— or —O—CO—; and k, l, m, n, o and p are zero or one provided that the sum k+m+o is greater than zero. The substances of the invention are characterized by a good temperature behavior of the nematic phase and good solubility.

13 Claims, No Drawings

3,4,5-TRIFLUOROBENZENES, AND THEIR USE IN LIQUID-CRYSTAL MIXTURES

DESCRIPTION

This application is a 371 of PCT/EP/94/032, filed Sep. 26, 1994.

The unusual combination of anisotropic and fluid behavior of liquid crystals has led to their use in electro-optical switching and display devices, where their electrical, magnetic, elastic and/or thermal properties can be utilized for changes in alignment. Optical effects can be achieved, for example, with the aid of birefringence, the inclusion of dichroic dye molecules (guest-host mode) or light scattering.

Practical requirements are constantly increasing, not least because of the constantly increasing number of types of light valve (TN, STN, DSTN, TFT, ECB, DECB, DS, GH, PDLC, NCAP, SSFLC, DHF, SBF, etc). In addition to thermodynamic and electro-optical quantities, such as phase sequence and phase temperature range, refractive index, birefringence and dielectric anisotropy, response time, threshold voltage, steepness of the electro-optical characteristic line, elastic constants, electrical resistance, multiplexibility or pitch and/or polarization in chiral phases, the stability of liquid crystals to moisture, gases, temperature and electromagnetic radiation and to the materials with which they are in contact during and after the manufacturing process (for example alignment layers) is of considerable importance. Toxicological and ecological acceptability and price are increasing in importance.

A broad review of the area of liquid crystals is given, for example, in the following literature and in the references cited therein: H. Kelker, H. Hatz, Handbook of Liquid Crystals, Verlag Chemie, Weinheim, 1980; W. E. De Jeu, Physical Properties of Liquid Crystal Materials, Gordon and Breach, Philadelphia 1980; H. Kresse, Dielectric Behaviour of Liquid Crystals, Fortschritte der Physik, Berlin 1982, 30, 507–582; B. Bahadur, Liquid Crystals: Applications and Uses, World Scientific, Singapore, 1990; Landolt-Börnstein, New Series, Group IV, Volume 7 Liquid Crystals 1992–1993.

Specific derivatives of 3,4,5-trifluorobenzene and their use in nematic liquid-crystal mixtures are known (cf. DE-A 41 08 448, GB-A 2 253 403, EP-A 507 094, EP-A 502 406, DE-A 41 39 553, WO-A 92/06 148, DE-A 41 12 001, DE-A 41 07 389, EP-A 387 032).

However, since individual compounds have hitherto not been able simultaneously to satisfy all said requirements, there is a continuing demand for novel improved liquid-crystal mixtures and thus for a multiplicity of mesogenic and nonmesogenic compounds of various structures which enable the mixtures to be customized to a wide variety of applications.

Surprisingly, it has now been found that certain derivatives of 3,4,5-trifluorobenzene are particularly suitable for use in liquid-crystal mixtures.

The present invention therefore relates to novel 3,4,5-trifluorobenzene derivatives of the formula (I).

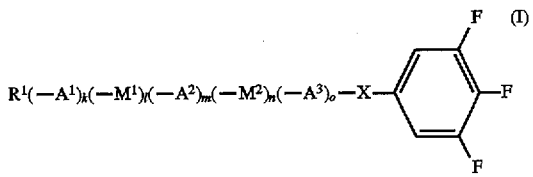

in which the symbols and indices have the following meanings:

$R^1$ is H, a straight-chain or branched (with or without an asymmetrical carbon atom) alkyl having 1 to 15 carbon atoms in which, in addition, one or two nonadjacent $-CH_2-$groups may be replaced by $-O-$, $CH=CH-$, $-C\equiv C-$, cyclopropane-1,2-diyl or $-Si(CH_3)_2-$, and in which, in addition, one or more H atoms in the alkyl radical may be substituted by F;

$A^1$, $A^2$ and $A^3$ are identical or different 1,4-phenylene, pyridine-2,5-diyl, pyrimidine-2,5-diyl in which one or two H atoms may be replaced by F, trans-1,4-cyclohexylene, 1,3-dioxane-2,5-diyl or naphthalene-2,6-diyl, $M^1$ and $M^2$ are identical or different $-CH_2CH_2-$, $-CH=CH-$, $-C\equiv C-$, $-CH_2CH_2CH_2-$, $-CH_2CH_2CH_2-O-$, $-O-CH_2CH_2CH_2-$, $-CH_2CH_2CO-O-$, $-O-CO-CH_2CH_2-$, $-CH_2-O-$, $-O-CH_2-$, $-CO-O-$ or $-O-CO-$;

X is $-CH_2-O-$, $-O-CH_2-$ or $-O-CO-$;

k, l, m, n, o are zero or one, with the proviso that the sum k+m+o is greater than zero.

The novel substances are distinguished by a favorable temperature position of the nematic phase and by good solubility.

In a preferred embodiment of the invention, the symbols and indices in the formula (I) have the following meanings:

$R^1$ is a straight-chain alkyl having 1 to 15 carbon atoms;

$A^1$, $A^2$ and $A^3$ are identical or different 1,4-phenylene in which one or two H atoms may be replaced by F, or trans- 1,4-cyclohexylene;

$M^1$ and $M^2$ are identical or different $-CH_2CH_2-$, $-C\equiv C-$, $-CH_2-O-$, $-O-CH_2-$, $-CO-O-$ or $-O-CO-$;

X is $-CH_2-O-$, $-O-CH_2-$ or $-O-CO-$;

k, l, m, n and o are zero or one, with the proviso that the sum k+m+o is greater than zero.

Particular preference is given to the 3,4,5-trifluorobenzenes of the formula (I) shown below in the formulae (I1) to (I5):

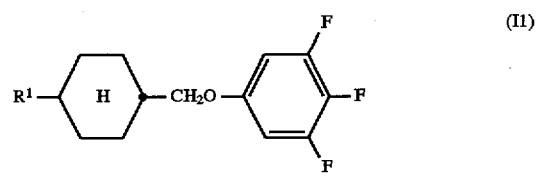

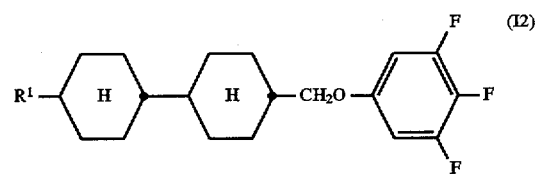

-continued

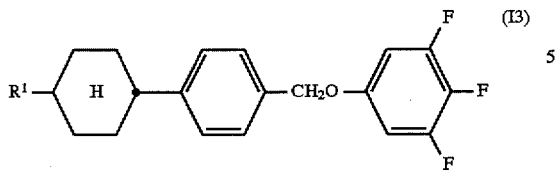

Esterification of 3,4,5-trifluorobenzoic acid (IV) using alcohols of $Z^1$ likewise gives novel compounds of the formula (I).

Regarding performance of the syntheses, see, inter alia:

Journal of the American Chemical Society 1947, 69, 2451;

Synthesis 1981, 1;

Tetrahedron 1980, 36, 2409.

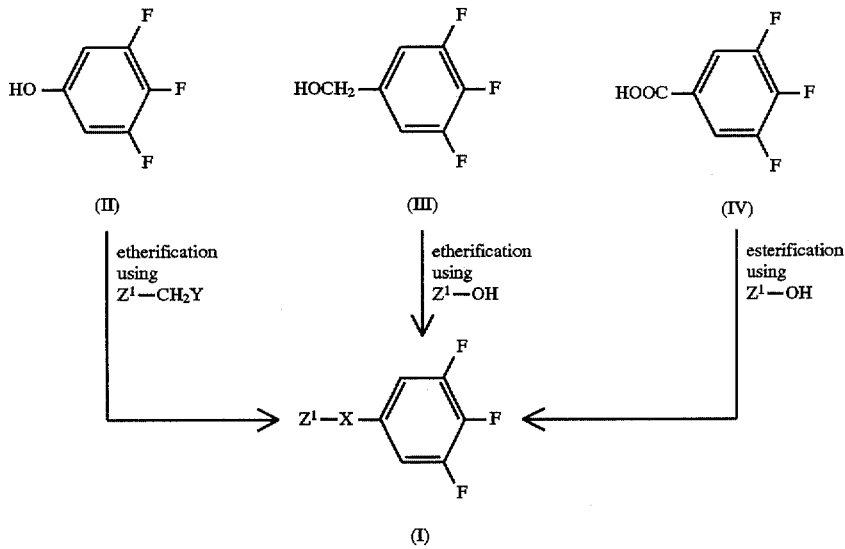

-continued

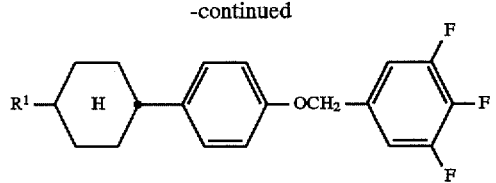

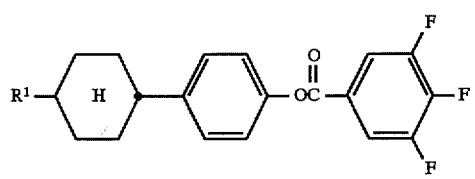

where $R^1$ is methyl, ethyl, propyl, buryl, pentyl, hexyl, heptyl, octyl, nonyl or decyl.

The novel compounds can be prepared by methods known from the literature (see, for example, Houben-Weyl, Methoden der Organischen Chemie [Methods of Organic Chemistry], Georg Thieme Verlag, Stuttgart).

Excellent starting compounds for the synthesis, illustrated in scheme 1, of the novel 3,4,5-trifluoro- benzenes are 3,4,5-trifluorophenol (II), 3,4,5-trifluoro- benzyl alcohol (III) and 3,4,5-trifluorobenzoic acid (IV).

Starting from 3,4,5-trifluorophenol (II), species of the formula (I) are obtained by etherification using hydroxymethyl or halomethyl derivatives of $Z^1$.

Etherification of 3,4,5-trifluorobenzyl alcohol (III) using alcohols of $Z^1$ likewise gives compounds of the formula (I).

[Veretherung mit=etherification using, Veresterung mit=esterification using]

Y=OH, Cl or Br
$Z^1=R^1(-A^1)_k(-M^1)_1(-A^2)_m(-M^2)_n(-A^3)_o$
X=—OCH$_2$—, —CH$_2$O— or —O—CO—

The $R^1(-A^1)_k(-M^1)_l(-A^2)_m(-M^2)_n(-A^3)_o$ radical or a suitable precursor is synthesized by methods known per se and customary to the person skilled in the art.

The preparation is carried out under reaction conditions which are known and are suitable for said reactions. Use can also be made here of variants which are known per se and are not described here in greater detail.

For example, reference is made to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 0 391 203 for compounds containing pyridine-2,5-diyl groups; WO-A 92/16500 for naphthalene-2,6-diyl groups.

The preparation of disubstituted pyridines and disubstituted pyrimidines is also given, for example, in the appropriate volumes of the series "The Chemistry of Heterocyclic Compounds" by A. Weissberger and E. C. Taylor (editors).

Dioxane derivatives are expediently prepared by reaction of an appropriate aldehyde (or of one of its reactive derivatives) with an appropriate 1,3-diol (or one of its reactive derivatives), preferably in the presence of an inert solvent, such as benzene or toluene, and/or of a catalyst, for example a strong acid, such as sulfuric acid, benzene-or p-toluenesulfonic acid, at temperatures between about 20°

C. and about 150° C., preferably between 80° C. and 120° C. Suitable reactive derivatives of the starting materials are primarily acetals.

Some of said aldehydes and 1,3-diols and their reactive derivatives are known, and some can be prepared without difficulties by standard methods of organic chemistry from compounds known from the literature. For example, the aldehydes are obtainable by oxidation of corresponding alcohols or by reduction of nitriles or corresponding carboxylic acids or their derivatives, and the diols are obtainable by reduction of corresponding diesters.

Compounds in which an aromatic ring carries at least one F atom as substituent can also be obtained from the corresponding diazonium salts by exchange of the diazonium group by a fluorine atom, for example by the methods of Balz and Schiemann.

Regarding the linking of the ring systems to one another, reference is made, for example, to the following:

N. Miyaura, T. Yanagai and A. Suzuki, Synth. Comm. 1971, 11, 513–519; DE-C-39 30 663; M. J. Sharp, W. Cheng, V. Snieckus, Tetrahedron Letters 1987, 28, 5093; G. W. Gray, J. Chem. Soc. Perkin Trans II 1989, 2041 and Mol. Cryst. Liq. Cryst. 1988, 172, 165; 1991, 204, 43 and 91; EP-A 0 449 015; WO-A 89/12039; WO-A 89/03821 and EP-A 0 354 434 for the direct linking of aromatic and heteroaromatic rings; DE-A 32 01 721 for compounds containing —$CH_2CH_2$— bridges, and Koji Sero et al., Liquid Crystals 1990, 8, 861–870 for compounds containing —C≡C— bridges.

Esters of the formula (I) can also be obtained by esterification of appropriate carboxylic acids (or their reactive derivatives) using alcohols or phenols (or their reactive derivatives) or by the DCC method (DCC= dicyclohexylcarbodiimide).

The corresponding carboxylic acids and alcohols or phenols are known and can be prepared analogously to known processes.

Particularly suitable reactive derivatives of said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols or phenols are the corresponding metal alkoxides or phenoxides, preferably of an alkali metal, such as sodium or potassium.

The esterification is advantageously carried out in the presence of an inert solvent. Particularly suitable are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide, sulfonate or dialkyl sulfate, expediently in an inert solvent, such as acetone, 1,2-dimethoxyethane, DMF or dimethyl sulfoxide, or alternatively with an excess of aqueous or aqueous-alcoholic NaOH or KOH at temperatures between about 20° and 100° C.

Regarding the synthesis of specific radicals $R^1$, reference is additionally made, for example, to EP-A 0 355 008 for compounds with silicon-containing side chains and EP-A 0 292 954 and EP-A 0 398 155 for compounds with cyclopropyl groups in the side chain.

The novel compounds of the general formula (I) are chemically and photochemically stable. They have low melting points and generally have broad liquid-crystalline phases, in particular broad nematic phases.

Compounds of the formula (I) can be used, for example, for the preparation of nematic or alternatively chirally nematic liquid-crystal mixtures which are suitable for use in electro-optical or fully optical elements, for example display elements, switching elements, light modulators, elements for image processing, signal processing or generally in the area of nonlinear optics. This also applies to compounds which, as pure substance, have no liquid-crystalline phases. In general, the compounds of the formula (I) are suitable for introducing or broadening a nematic phase into or in LC mixtures.

The invention therefore also relates to the use of compounds of the formula (I) in liquid-crystal mixtures.

The invention furthermore relates to liquid- crystal mixtures which contain one or more compounds of the formula (I).

The novel liquid-crystal mixtures generally comprise from 2 to 20, preferably from 2 to 15, components, including at least one, preferably from 1 to 5, particularly preferably from 1 to 3, compounds of the formula (I). The novel LC mixtures can, for example, be nematic or chiral nematic. The liquid-crystal mixtures generally contain from 0.1 to 70 mol %, preferably from 0.5 to 50 mol %, in particular from 1 to 25 mol %, of the novel compounds of the formula (I).

Further constituents of the novel mixtures are preferably selected from those compounds having nematic or cholesteric phases these include, for example, biphenyls, terphenyls, phenylcyclohexanes, bicyclohexanes, cyclohexylbiphenyls, and mono-, di- and tri- fluorophenyls. In general, the commercially available liquid-crystal mixtures are already, before addition of the novel compound(s), in the form of mixtures of various components, of which at least one is mesogenic.

Further suitable constituents of novel nematic or chiral nematic liquid-crystal mixtures are, for example 4-fluorobenzenes, as described, for example, in EP-A 494 368, WO 92/06 148, EP-A 460 436, DE-A 4 111 766, DE-A 4 112 024, DE-A 4 112 001, DE-A 4 100 288, DE-A 4 101 468, EP-A 423 520, DE-A 392 3064, EP-A 406 468, EP-A 393 577 and EP-A 393 490, 3,4-difluorobenzenes, as described, for example, in DE-A 4 108 448, EP-A 507 094 and EP-A 502 407, 3,4,5-trifluorobenzene, as described, for example, in DE-A 4 108 448 and EP-A 387 032, 4-benzotrifluorides, as described, for example, in DE-A 4 108 448, phenylcyclohexanes, as described, for example, in DE-A 4 108 448.

Liquid-crystalline mixtures containing compounds of the general formula (I) are particularly suitable for use in electro-optical switching and display devices (displays). Such switching and display devices (LC displays) generally have, inter alia, the following constituents: a liquid-crystalline medium, outer plates (for example made of glass or plastic), coated with transparent electrodes, at least one alignment layer, spacers, adhesive frame, polarizers and, for color displays, thin color-filter layers. Further possible components are antireflection, passivation, compensation and barrier layers and electrically nonlinear elements, such as thin-film transistors (TFTs) and metal-insulator-metal (MIM) elements. The structure of liquid-crystal displays has already been described in detail in relevant monographs (for example E. Kaneko, "Liquid Crystal TV Displays: Principles and Applications of Liquid Crystal Displays", KTK Scientific Publishers, 1987, pages 12–30 and 63–172).

EXAMPLES

Various measurement methods are used for the physical characterization of the novel compounds.

The phase transition temperatures are determined using a polarizing microscope from the changes in structure during heating. By contrast, the melting point is determined using a DSC instrument. The phase transition temperatures between the phases

|               |                  |
| ------------- | ---------------- |
| isotropic     | (I)              |
| nematic       | (N or N*)        |
| smectic-C     | ($S_c$ or $S_c^*$) |
| smectic-A     | ($S_A$ or $S_A^*$) |
| crystalline   | (X)              |
| glass transition | (Tg)          | are given in °C., and the values are between the phase designations in the phase sequence.

If the values for heating and cooling are different, the latter are enclosed by parentheses, or the phase sequence with rising or falling temperature is given.

Electro-optical measurements are carried out by methods known from the literature (for example B. Bahadur: Liquid Crystals Application and Uses, Vol. I, World Scientific, Singapore, 1990).

For nematic liquid crystals (pure or in mixtures), the values for the optical and dielectric anisotropy and the electro-optical characteristic line are recorded at a temperature of 20° C.

Liquid crystals which do not have a nematic phase at 20° C. are mixed in an amount of 10% by weight into ZLI-1565 and/or to the extent of 20% by weight into ZLI-4792 (commercial nematic liquid-crystal mixtures from E. Merck, Darmstadt), and the values are extrapolated from the results for the mixture.

Electro-optical characteristic lines are determined from the transmission of a measurement cell. To this end, the cell is positioned between crossed polarizers in front of a light source. A light detector whose sensitivity has been optimized to the visible region of light by means of filters is positioned behind the cell. The change in transmission is recorded analogously to the stepwise increase in the voltage applied to the cell. Quantities such as threshold voltage and steepness are determined therefrom.

The optical anisotropy is determined using an Abbé refractometer (Zeiss). In order to align the liquid crystal, an alignment layer obtained from a 1% strength by weight lecithin/methanol solution is applied to the prism.

In order to determine the dielectric anisotropy, a measurement cell with a homeotropic and planar alignment is produced in each case and its capacitances and dielectric losses are determined using a multifrequency LCR meter (Hewlett Packard 4274 A). The dielectric constants are calculated as described in the literature (W. Maier, G. Meier, Z. Naturforsch. 1961, 16a, 262, and W. H. de Jeu, F. Leenhonts, J. Physique 1978, 39, 869). The electric quantity HR (holding ratio) is determined as described in the literature (M. Schadt, Linear and nonlinear liquid crystal materials, Liquid Crystals 1993, 14, 73–104).

In order to determine the response time (τ) and contrast (K), the measurement cell is clamped to the rotating stage of a polarizing microscope between crossed analyzer and polarizer. In order to determine the contrast, the measurement cell is positioned by rotation so that a photodiode shows minimal light transmission (dark state). The microscope illumination is adjusted so that the photodiode shows the same light intensity for all cells. After a switching operation, the light intensity changes (bright state), and the contrast is calculated from the ratio between the light intensities in these states.

Example 1

3,4,5-Trifluorophenyl (trans-4-pentylcyclohexyl)methyl ether 1.31 g (7.5 mmol) of diethyl azodicarboxylate are added at 0° C. to 1.97 g (7.50 mmol) of triphenylphosphine in 30 ml of tetrahydrofuran, and the mixture is stirred at room temperature for 0.5 hour. 1.11 g (7.50 mmol) of 3,4,5-trifluorophenol and 1.38 g (7.50 mmol) of trans-4-pentylcyclohexylmethanol are then added, and the mixture is stirred at room temperature for 18 hours. Evaporation of the solvent and chromatography on silica gel using hexane give 1.23 g of product.

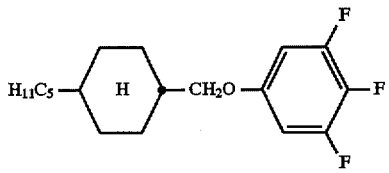

Phase sequence: X 14 (–26) I

The following are prepared analogously to Example 1:

Example 2

3,4,5-Trifluorophenyl (trans-4-ethylcyclohexyl)methyl ether

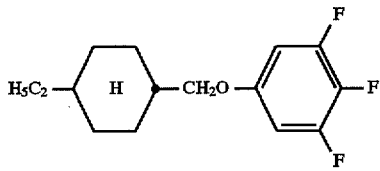

Example 3

3,4,5-Trifluorophenyl (trans-4-propylcyclohexyl)methyl ether

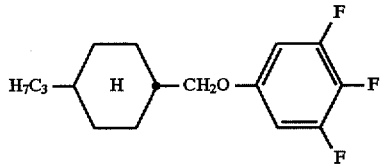

Example 4

3,4,5-Trifluorophenyl (trans-4-butylcyclohexyl)methyl ether

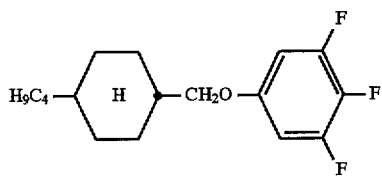

Example 5

3,4,5-Trifluorophenyl [trans-4(trans-4-ethycyclohexyl)-cyclohexyl]methyl ether

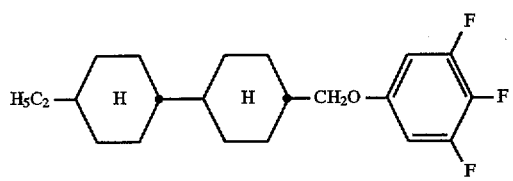

Example 6

3,4,5-Trifluorophenyl [trans-4-(trans-4-propylcyclohexyl)cyclohexyl]methyl ether

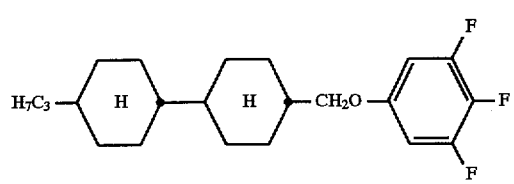

Example 7

3,4,5-Trifluorophenyl [trans-4-(trans-4-butylcyclohexyl)-cyclohexyl]methyl ether

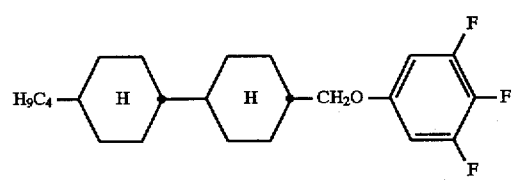

Example 8

3,4,5-Trifluorophenyl [trans-4-(trans-4-pentylcyclohexyl)cyclohexyl]methyl ether

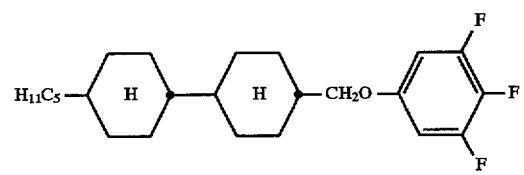

Phase sequence X 73 (49) N 89 I

Example 9

3,4,5-Trifluorophenyl [4-(trans-4-ethylcyclohexyl)phenyl]methyl ether

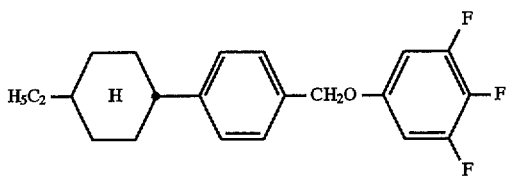

Example 10

3,4,5-Trifluorophenyl [4-(trans-4-propylcyclohexyl)-phenyl]methyl ether

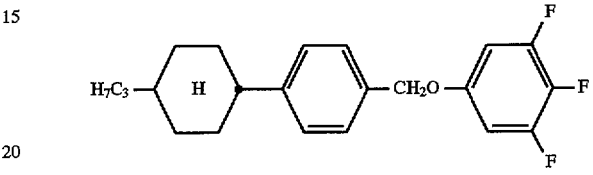

Example 11

3,4,5-Trifluorophenyl [4-(trans-4-butylcyclohexyl)-phenyl] methyl ether

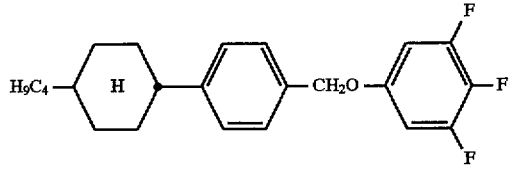

Example 12

3,4,5-Trifluorophenyl [4-(trans-4-pentylcyclohexyl)-phenyl]methyl ether

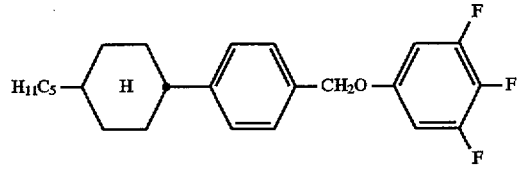

Phase sequence: X 39 (−5) I

Example 13

3,4,5-Trifluorophenylmethyl [4-(trans-4-ethylcyclohexyl)-phenyl]ether

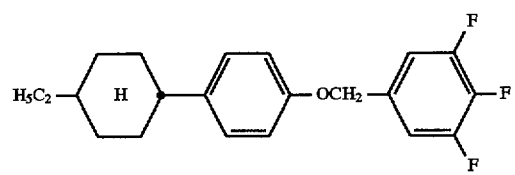

Phase sequence: X 41 (20) I

Example 14

3,4,5-Trifluorophenylmethyl [4-(trans-4-propylcyclohexyl) phenyl] ether

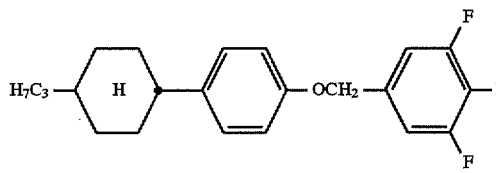

Phase sequence: X 70 (33) I

Example 15

3,4,5-Trifluorophenylmethyl [4-(trans-4-butylcyclohexyl)-phenyl] ether

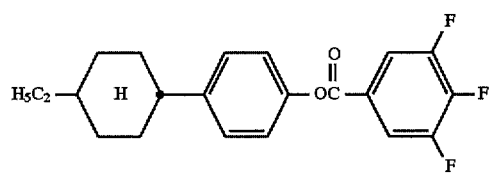

Phase sequence: X 58 (22) I

Example 16

3,4,5-Trifluorophenylmethyl [4-(trans-4-pentylcyclohexyl)phenyl] ether

Phase sequence: X 54 (24) N (37) I

Example 17

4-(Trans-4-ethylcyclohexyl)phenyl 3,4,5-trifluorobenzoate 1.03 g (5.00 mmol) of dicyclohexylcarbodiimide, 0.88 g (5.00 mmol) of 3,4,5-trifluorobenzoic acid and 1.02 g (5.00 mmol) of 4-(trans-4-ethylcyclohexyl)phenol are stirred at room temperature for 6 hours with 10 mg of 4-N,N-dimethylaminopyridine in 30 ml of dichloromethane. Filtration, evaporation of the solvent and purification by chromatography (silica gel/hexane) give 1.36 g of product.

Phase sequence: X 90 (59) N (72) I

The following are prepared analogously to Example 17

Example 18

4-(Trans-4-propylcyclohexyl)phenyl 3,4,5-trifluorobenzoate

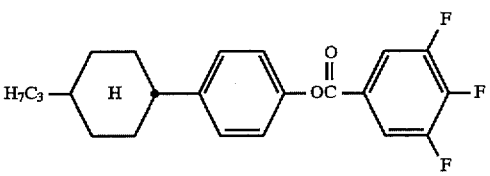

Phase sequence: $X_1$ 79 $X_2$ 98(64) N 105 I

Example 19

4-(Trans-4-butylcyclohexyl)phenyl 3,4,5-trifluorobenzoate

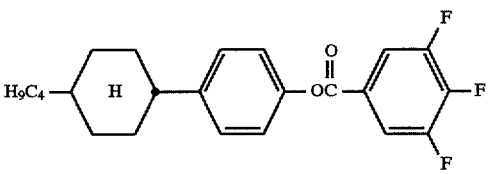

Phase sequence: X 104 (59) $S_x$ (65) N 104 I

Example 20

4-(Trans-4-pentylcyclohexyl)phenyl 3,4,5-trifluorobenzoate

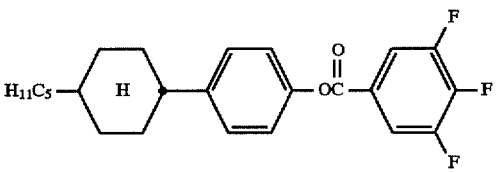

Phase sequence: X 99 (69) N 113 I

Use Examples

The table compares the novel substance from Example 20 with known references, both as pure substance and in a mixture with ZLI-4792 (commercial nematic liquid-crystal mixture from E. Merck, Darmstadt).

The substance from Example 20 has a broad nematic phase with a significantly higher clearing point, which is favorable.

In a mixture too, it is found that the clearing point of the starting mixture is advantageously raised, while the references lower the clearing point. In addition, the novel substance does not raise the melting point of the mixture as much as the references.

TABLE

| | Pure substance Phases/°C. | 20% by weight in ZLI-4792 Phases/°C. |
|---|---|---|
| Subst. from Example 20 | X 99 (69) N 113 I | Tg (−82) S$_X$- 60 (−63) X$_{re}$- 35 X 36 N 97 I |
| Reference from EP 387032 | X 91 (74) N 99 I | Tg (−81) X$_{re}$- 54 X 52 N 93 I |
| Reference from EP 387932 | X 29 (0) N 55 I | Tg (−84) X$_{re}$- 74 X 60 N 89 I |
| ZLI-4792 MERCK, Darmstadt | | Tg (−84) X$_{re}$- 63 X- 31/−9 S$_X$ (−44) N 94 I |

We claim:

1. A 3,4,5-trifluorobenzene compound of the formula (I)

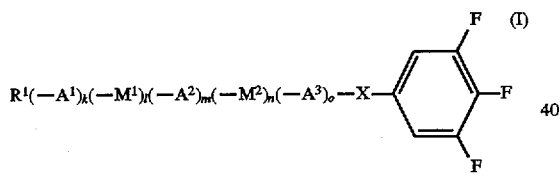

in which

R$^1$ is a straight-chain or branched alkyl having 1 to 15 carbon atoms in which, optionally, one or two nonadjacent —CH$_2$—groups are replaced by —O—, —CH═CH—, —C≡C—, cyclopropane-1,2-diyl or —Si(CH$_3$)$_2$—, and in which, optionally, one or more H atoms in the alkyl radical may be substituted by F;

A$^1$, A$^2$ and A$^3$ are identical or different 1,4-phenylene, pyridine-2,5-diyl, pyrimidine-2,5-diyl in which one or two H atoms are optionally replaced by F, trans-1,4-cyclohexylene, 1,3-dioxane-2,5-diyl or naphthalene-2,6-diyl, M$^1$ and M$^2$ are identical or different —CH$_2$CH$_2$—,— CH═CH—,—C≡C—,—CH$_2$CH$_2$CH$_2$—CH$_2$—, —CH$_2$—O—,—O—CH$_2$—, —CO—O— or —O—CO;

X is —CH$_2$—O—,—OCH$_2$— or —O—CO—; and k, l, m, n are zero or one.

2. A 3,4,5-trifluorbenzene according to claim 1 wherein:

R$^1$ is a straight-chain alkyl having 1 to 15 carbon atoms;

A$^1$, A$^2$ and A$^3$ are identical or different 1,4-phenylene in which one to two H atoms are optionally replaced by F, or trans-1,4-cyclohexylene;

M$^1$ and M$^2$ are identical or different —CH$_2$CH$_2$—,— C≡C—,—CH$_2$—O—,—OCH$_2$—,—CO—O— or —O—CO;

X is —CH$_2$—O—,—OCH$_2$— or —O—CO—; and k, l, m, n are zero or one.

3. A 3,4,5-trifluorobenzene compound of one of the formulae (I1 to I5):

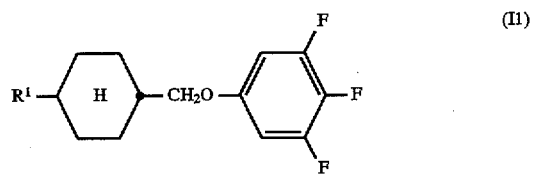

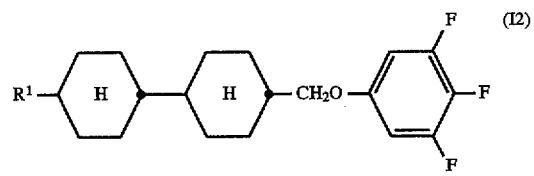

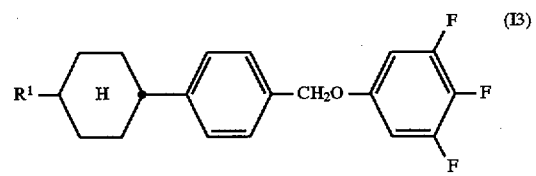

-continued

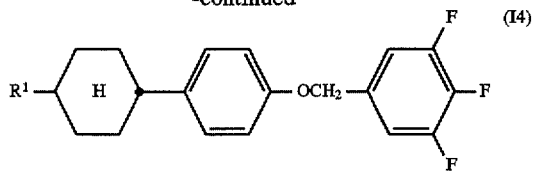

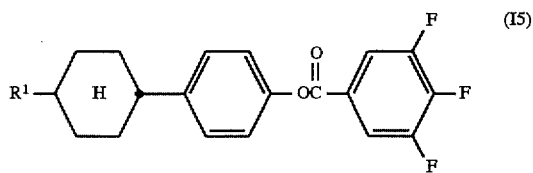

where

R¹ is methyl, ethyl, propyl, butyl, pentyl, hexyl, heptyl, octyl, nonyl or decyl.

4. Liquid-crystal mixture containing at least one compound of the formula (I) according to claim 1.

5. Liquid-crystal mixture according to claim 4, wherein the liquid-crystal mixture is nematic.

6. Liquid-crystal mixture according to claim 5 which contains from 1 to 8 compounds of the formula (I).

7. Liquid-crystal mixture according to claim 5 which contains from 0.1 to 70 mol % of at least one compound of the formula (I).

8. Switching and/or display device, containing outer plates, electrodes, at least one polarizer, at least one alignment layer and a liquid-crystalline medium, wherein liquid-crystalline medium is a liquid-crystal mixture according to claim 5.

9. A switching and/or display device containing outer plates, electrodes, at least one polarizer, at least one alignment layer and a liquid crystalline medium, wherein the liquid crystalline medium is a liquid-crystal mixture according to claim 5.

10. A switching and/or display device containing outer plates, electrodes, at least one polarizer, at least one alignment layer and a liquid crystalline medium, wherein the liquid crystalline medium is a liquid-crystal mixture according to claim 6.

11. A switching and/or display device containing outer plates, electrodes, at least one polarizer, at least one alignment layer and a liquid crystalline medium, wherein the liquid crystalline medium is a liquid-crystal mixture according to claim 7.

12. A liquid-crystal mixture comprising at least one compound of one of the formulae (I1) to (I5) according to claim 3.

13. A switching and/or display device containing outer plates, electrodes, at least one polarizer, at least one alignment layer and a liquid crystalline medium, wherein the liquid crystalline medium is a liquid-crystal mixture according to claim 12.

* * * * *